United States Patent [19]

Greenfield et al.

[11] Patent Number: 5,677,344
[45] Date of Patent: Oct. 14, 1997

[54] METHOD FOR TREATING PARKINSON'S DISEASE EMPLOYING AN ATP-SENSITIVE POTASSIUM CHANNEL BLOCKER

[75] Inventors: Susan A. Greenfield, Oxford, England; Denyse Levesque, Chandler, Canada

[73] Assignee: E. R. Squibb & Sons, Inc., Princeton, N.Y.

[21] Appl. No.: 65,792

[22] Filed: May 24, 1993

Related U.S. Application Data

[63] Continuation of Ser. No. 554,772, Jul. 19, 1990, abandoned.
[51] Int. Cl.$^6$ .................... A61K 31/55; A61K 31/495; A61K 31/175
[52] U.S. Cl. .................. 514/592; 514/212; 514/255; 514/593
[58] Field of Search ................... 514/212, 255, 514/592, 593

[56] References Cited

PUBLICATIONS

Noma A. (1983), "ATP-regulated K$^+$ channels in cardiac muscle" Nature 305: 147–148.
Kakei M. and Noma A. (1984) "Adenosine 5'–triphosphate–sensitive single potassium channel in the atrioventricular node cell of the rabbit heart," J. Physiol. 352: 265–284.
Ashcrfot, F.M. et al (1984), "Glucose induced closure of single potassium channels in isolated rat pancreatic β–cells," Nature 312: 446–448.

Sturgess, N.C. et al (1985), "The sulphonylurea receptor may be an ATP–sensitive potassium channel," Lancet 8435: 474–475.
Standen, N.B. et al (1989), "Hyperpolarizing vasodilators activate ATP–sensitive K$^+$ channels in arterial smooth muscle," Science 245: 177–180.
Mourre, C. et al (1989), "Antidiabetic sulfonylureas: localization of binding sites in the brain and effects on the hyperpolarization induced by anoxia in hippocampal slices," Brain Res. 486: 159–164.
Virsolvyl–Vergine, A. et al (1988), "An endogenous ligand for the central sulfonylurea receptor," FEBS Letters 242: 65–69.
Ungerstedt, U. (1971), "Striatal dopamine release after amphetamine or nerve degeneration revealed by rotational behaviour," Acta Physiol. Scand. Suppl. 367: 49–68.
Greenfield, S.A. et al (1984), "A noncholinergic function for acetylcholinesterase in the substantia nigra:behavioural evidence," Expt. Brain Res. 54: 513–520.
Hansen et al., "Tolbatamide in the Treatment of Parkinson's Disease A Double Blind Trial", Danish Medical Bulletin, Dec. 1965, vol. 12, No. 7–8, pp. 181–184.

*Primary Examiner*—Kimberly Jordan
*Attorney, Agent, or Firm*—Burton Rodney

[57] ABSTRACT

A method is provided for treatment of Parkinson's disease or controlling movement of a Parkinsonian patient by administering an ATP-sensitive potassium channel blocker, such as a sulfonyl urea, (for example, tolbutamide), or quinine.

15 Claims, 2 Drawing Sheets

METHOD FOR TREATING PARKINSON'S DISEASE EMPLOYING AN ATP-SENSITIVE POTASSIUM CHANNEL BLOCKER

This is a continuation of application Ser. No. 07/554,772, filed Jul. 19, 1990, now abandoned.

FIELD OF THE INVENTION

The present invention relates to a method for treating Parkinson's disease or controlling movement of a Parkinsonian patient by administering an ATP-sensitive potassium channel blocker.

BACKGROUND OF THE INVENTION

A species of potassium channel that is dependent on adenosine triphosphate (ATP) was first described in cardiac muscle by Noma A. (1983), "ATP-regulated $K^+$ channels in cardiac muscle," Nature 305: 147–148. This channel has attracted increasing interest due to its unusual and close association with cell metabolism. Ashcroft, F. M. (1988), "Adenosine 5-triphosphate-sensitive potassium channels," Ann. Rev. Neurosci. 11: 97–118. It is now well established that ATP-sensitive potassium channels are present in diverse tissues i.e. cardiac muscle, (Kakei M. and Noma A. (1984) "Adenosine 5'-triphosphate-sensitive single potassium channel in the atrioventricular node cell of the rabbit heart," J. Physiol. 352: 265–284, Noma A. and Shibasake, T. (1985), "Membrane current through adenosine-triphosphate-regulated potassium channels in guinea-pig ventricular cells," J. Physiol. 363: 463–480), pancreatic beta cells (Findlay, I., Dunne, M. J., and Petersen, O. H. (1985a), "ATP-sensitive inward rectifier and voltage- and calcium activated $K^+$ channels in cultured pancreatic islet cells," J. Memb. Biol. 88: 165–172; Dunne, M. J., Findlay, I., Petersen, O. H. and Wollheim, C. B. (1986), "ATP-sensitive $K^+$ channels in an insulin-secreting cell line are inhibited by D-glyceraldehyde and activated by membrane permeabilization." J. Memb. Biol. 93: 271–279; Ashcroft, F. M. et al (1984), "Glucose induces closure of single potassium channels in isolated rat pancreatic β-cells," Nature 312: 446–448); skeletal muscle (Sturgess, N. C., Ashford, M. L. J., Cook, D. L. and Hales, C. N. (1985), "The sulphonylurea receptor may be an ATP-sensitive potassium channel," Lancet 8435: 474–475) and smooth muscle (Standen, N. B., Quayle, J. M., Davies, N. W., Brayden, J. E., Huang, Y. and Nelson, M. T. (1989), "Hyperpolarizing vasodilators activate ATP-sensitive $K^+$ channels in arterial smooth muscle," Science 245: 177–180). More recently, indirect evidence has suggested that the ATP-sensitive channel may also be present in the brain: sulfonylureas, which are potent blocking agents of this channel in heart and beta cells, display selective binding in certain brain regions (Mourre, C., Ben Ari, Y., Bernardi, H., Fosset, M. and Lazdunski, M. (1989), "Antidiabetic sulfonylureas: localization of binding sites in the brain and effects on the hyperpolarization induced by anoxia in hippocampal slices," Brain Res. 486: 159–164) and indeed an endogenous ligand for a central sulfonylurea receptor has been described (Virsolvy-Vergine, A., Bruck, M., Dufour, M., Cauvin, A., Lupo, B. and Bataille, D. (1988), "An endogenous ligand for the central sulfonylurea receptor," FEBS Letters 242: 65–69). It has also been found that sulfonylurea binding sites appear to be highest in regions of the brain associated with the control of movement, i.e. motor cortex, cerebellar cortex, globus pallidus and substantia nigra (Mourre et al., supra, 1989).

It is well known that disparities in the availability of dopamine (DA) between the two nigrostriatal systems leads to circling behaviour in a direction towards the side of dopamine deficiency (Ungerstedt, U. (1971), "Striatal dopamine release after amphetamine or nerve degeneration revealed by rotational behaviour," Acta Physiol, Scand. Suppl. 367: 49–68). This model has previously proved valuable in assessing the action of putative neuroactive agents, i.e. substances introduced locally into the substantia nigra can initiate circling behaviour in otherwise normal rats (Greenfield, S. A., Chubb, I. W., Grunewald, R. A., Henderson, Z., May J., Portnoy, S., Weston J. and Wright, M. D. (1984), "A non-cholinergic function for acetylcholinesterase in the substantia nigra:behavioural evidence," Expt. Brain Res. 54: 513–520).

DESCRIPTION OF THE INVENTION

In Parkinson's disease, a portion of the neurons in the brain which is important in the regulation of movement has been found to degenerate. This portion of the neurons contains a pore or channel in the membrane that lets potassium out of the cell, under certain conditions relating to the metabolism in the neuron ("K-ATP channel"). In accordance with the present invention, by administering to the brain of a Parkinsonian patient, especially the substantia nigra portion, thereof, a substance which blocks the K-ATP channel, otherwise uncontrollable movements of the patients may be controlled.

In accordance with the present invention, a method is provided for treating Parkinson's disease wherein a therapeutically effective amount of a pharmaceutical which blocks an ATP-sensitive potassium channel in the brain is administered to a mammalian species in need of such treatment.

In addition, in accordance with the present invention, a method is provided for controlling movement of a Parkinsonian patient, wherein a therapeutically effective amount of a pharmaceutical which blocks the ATP-sensitive potassium channel in the substantial nigra is administered to modify the net activity of the nigrostriatal pathway to control movement.

The pharmaceutical employed in the methods of the present invention will be an effective blocker of the ATP-sensitive potassium channel in the brain. Examples of such a pharmaceutical include, but are not limited to sulfonyl ureas such as glyburide (1-[[p-[2-(5-chloro-O-anisamido)-ethyl]phenyl]sulfonyl]-3-cyclohexylurea); chloropropamide (1-[(p-chlorophenyl)sulfonyl]-3-propylurea); glipizide(1-cyclohexyl-3-[[p-[2-(5-methyl-pyrazine-carboximido)ethyl] phenyl]sulfonyl]urea); tolazamide-(benzenesulfonamide-N-[[(hexahydro-1H-azepin-1-yl)-amino]-carbonyl,-4-methyl), or tolbutamide (benzene-sulfoamide,N-(butylamino) carbonyl]-4-methyl), with the latter being preferred. In addition, quinine may also be employed in place of the sulfonyl urea.

Although the K-ATP channel blocker employed in the methods of the invention may be administered systemically, such as orally or parenterally, it is preferred that the K-ATP channel blocker be administered locally, for example, by carotid injection, lumbar puncture or cisternal puncture. The K-ATP blocker will be administered for as long as a treatment for Parkinson's disease or control of movement in Parkinsonian patients is required.

With regard to dosage of K-ATP channel blocker, where a wide region of the brain is to be treated, for example, by intracarotid injection, lumbar puncture or cisternal puncture, from about 0.1 to about 20 mg/kg/treatment and preferably from about 0.5 to about 15 mg/kg/treatment will be employed, depending upon the particular K-ATP channel blocker employed.

Where the K-ATP channel blocker is to be administered sytemically, such as orally or parenterally, it will be administered in an amount to achieve a steady state level of K-ATP channel blocker in the blood. Thus, for systemic treatment, the K-ATP channel blocker may be administered in an amount within the range of from about 0.5 to about 20 mg/kg for each treatment and preferably from about 1 to about 15 mg/kg for each treatment.

In carrying out the method of the present invention, the K-ATP channel blocker may be administered to mammalian species, such as monkeys, dogs, cats, rats, and humans. The K-ATP channel blocker may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

Figure 1:
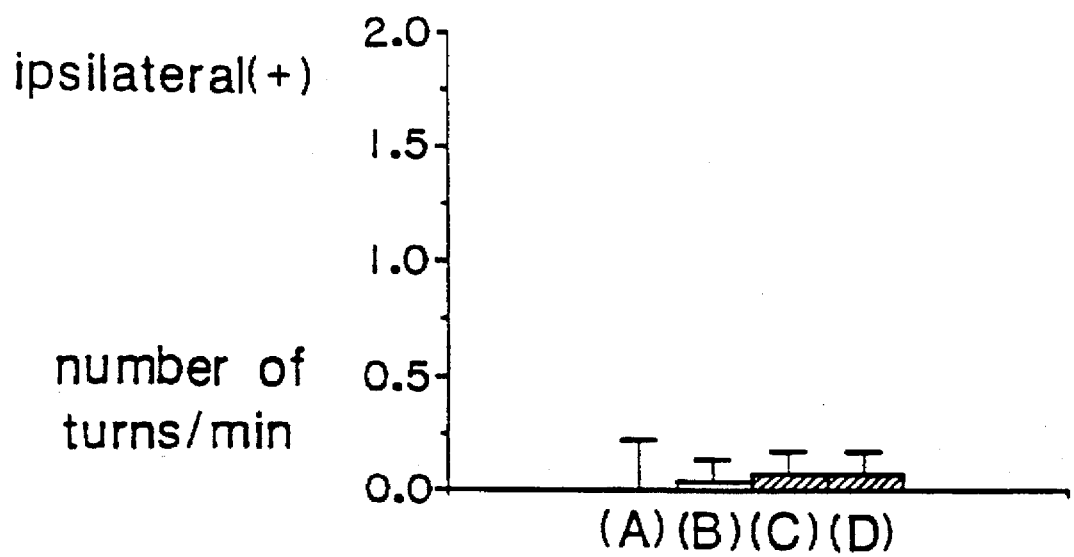
FIG. 1 is a graph which shows the effects of tetraethylammonium on circling behavior in the rat, as described in Example 5.

The following Examples represent preferred embodiments of the present invention.

EXAMPLE 1

An injectable solution for use in administering tolbutamide by injection in the carotid artery or by lumbar puncture for treating Parkinson's disease is produced as follows:

| Tolbutamide | 250 mg |
|---|---|
| Sodium chloride | 25 mg |
| Polyethylene glycol 400 | 1.5 l |
| Water for injection qs. | 5 l. |

The tolbutamide and sodium chloride are dissolved in 1.5 liters of polyethylene glycol 400 and 3 liters of water for injection and then the volume is brought up to 6.5 liters. The solution is filtered through a sterile filter and aseptically filled into presterilized vials which are then closed with presterilized rubber closures. Each vial contains 25 ml of solution in a concentration of 50 mg of active ingredient per ml of solution for injection.

EXAMPLE 2

An injectable for use in treating Parkinson's disease is prepared as described in Example 1 except that quinine is employed in place of tolbutamide.

EXAMPLE 3 and 4

An injectable for use in treating Parkinson's disease is prepared as described in Example 1 except that glyburide or glipizide is employed in place of tolbutamide.

EXAMPLE 5

Recent evidence suggests that an APT-sensitive potassium channel is present in the brain. From ligand binding studies it has been inferred that this relatively unfamiliar channel is particulary densely distributed in areas associated with motor control. The purpose of this study was thus to examine whether pharmacological agents specific for the ATP-sensitive channel in other tissues had effects on a particular motor behaviour associated with the substantia nigra: the effects of microinfusion into the substantia nigra of diverse potassium channel blocking agents were examined on initiation of circling behaviour in the normal rat.

The effects of microinfusion into the substantia nigra of substances known to block the ATP-sensitive potassium channel i.e. the sulfonylurea tolbutamide and quinine (Ashcroft, supra, 1988) were examined on the motor behaviour of the freely moving rat. These effects were compared with those of a classic general blocking agent of most potassium channels, which is nonetheless not very efficacious at inhibiting the ATP-sensitive potassium channel i.e. tetraethylammonium chloride (TEA) (Findlay et al., 1985b).

MATERIALS AND METHODS

Animal Preparation

Guide cannulae (Plastic Products Co) were implanted unilaterally in the region of the substantia nigra of surgically anaesthetized 250 g male Wistar rats (AP: −5.0; L: −2.2; DV: −7.0; skull levelled between bregma and lambda; Paxinos and Watson. The animals were then left for twenty-four hours to allow full recovery from surgery.

Infusion Procedure

In order to infuse solutions, a dummy cannula was replaced by an internal cannula (Plastic Products Co) within the implanted guide cannula such that it protruded 0.5 mm approximately. Solutions were infused through the internal cannula connected to a 10 µl Hamilton syringe by inert capillary tubing (0.010"I.D.) and driven by an automatic pump at a rate of 1 µl/10 min. After 10 min the pump was switched off but the internal cannula left in place for a subsequent minute. During infusion rats were freely-moving in a restricted area.

Assessment of Circling Behaviour (i) Test for circling prior to drug infusion:

Before implantation of the guide cannula, all rats were tested for any inherent bias: 10 min following administration of d-amphetamine sulphate (5 mg/kg i.p.) they were placed in a circular bowl (12 inches dia.) and the net number of 360° turns/min noted for 20 min. Animals with a mean score of 2 turns/min or more were not used further. The remaining rats were then implanted with an outer cannula in one substantia nigra. After full recovery from surgery, the rats were placed on two occasions in the bowl to habituate them to the environment. Following that they were tested for circling as described above to ascertain whether the implant itself caused a bias in direction of movement. Again animals with a mean score of 2 turns/min or more were not used further.

(ii) Test for circling behaviour post-drug infusion:

All rats were given two microinfusions, one of drug and one of vehicle solution: however half received drugs before control infusion whilst the remainder were given the vehicle first. Hence any artefactual effect resulting from mechanical stimulation or tissue scarring could be identified. Infusions were performed over ten minutes and were followed immediately by administration of amphetamine: rotation was observed ten minutes after this procedure for the subsequent twenty minutes. In order to ascertain whether the infusions had any lasting effects, all rats were again challenged with amphetamine the following day and tests for rotation performed as described above. When the rats displayed the pre-infusion circling score, the two groups were interchanged, i.e. animals previously given drug received control and vice-versa and the subsequent procedure was repeated as outlined above.

Drug Solutions

All drugs were infused in a volume of 1 μl. Quinine hydrochloride (Sigma, $1\times10^{-4}M$), and tetraethylammonium chloride (TEA) (Sigma, $1\times10^{-2}M$) were administered in a vehicle of NaCl (0.9% w/v). For tolbutamide (Sigma, $2.5\times10^{-4}M$), there was used NaCl (0.9% w/v) plus DMSO (Sigma, 0.5M stock solution) so that the powder would dissolve more readily.

Histological Procedures

At the end of the experiment, the animals were deeply anaesthetised and perfused with formaldehyde. The brains were removed and placed in formaldehyde and sucrose for at least twenty-four hours prior to sectioning. Cannulae placement within the substantia nigra were verified by examination of (50 μm) frozen cut sections, stained with cresyl violet. Placements were classified 'blind' by an outside observer as in pars compacta or pars reticulata. Any cases where the cannulae were aberrantly placed were discarded.

Reasons for Elimination of Data

In addition to those mentioned above, approximately twenty further rats were discarded from the study, for the following reasons: ill health post surgery, intra-cerebral haemmoragh, blockage in infusion pump or guide cannula. Furthermore it was occasionally observed that some rats did not display circling behaviour, even though there was no obvious reason (as above).

Analysis

Figure 3:
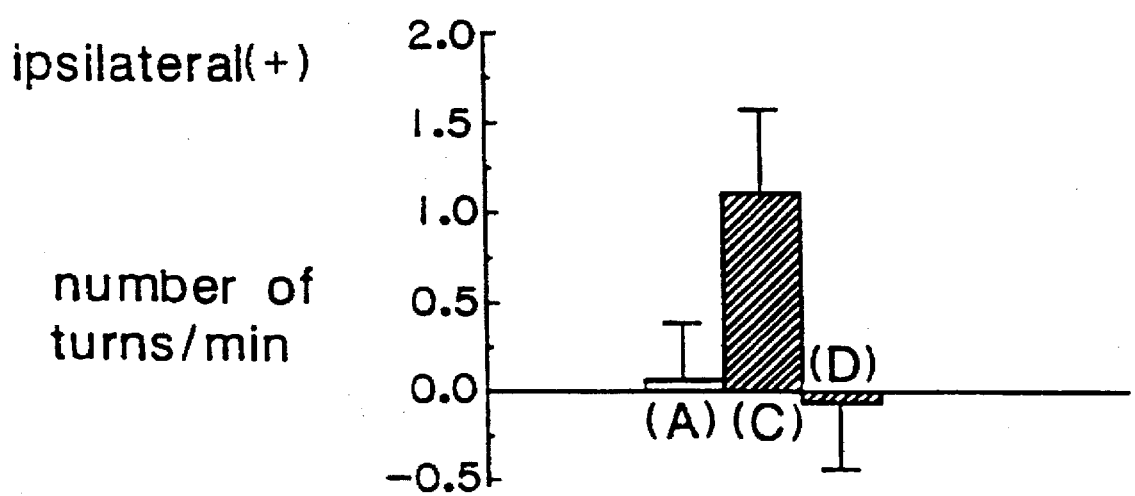
FIG. 3 shows the effects of quinine on circling behavior, as described in Example 5.
Figure 2A:
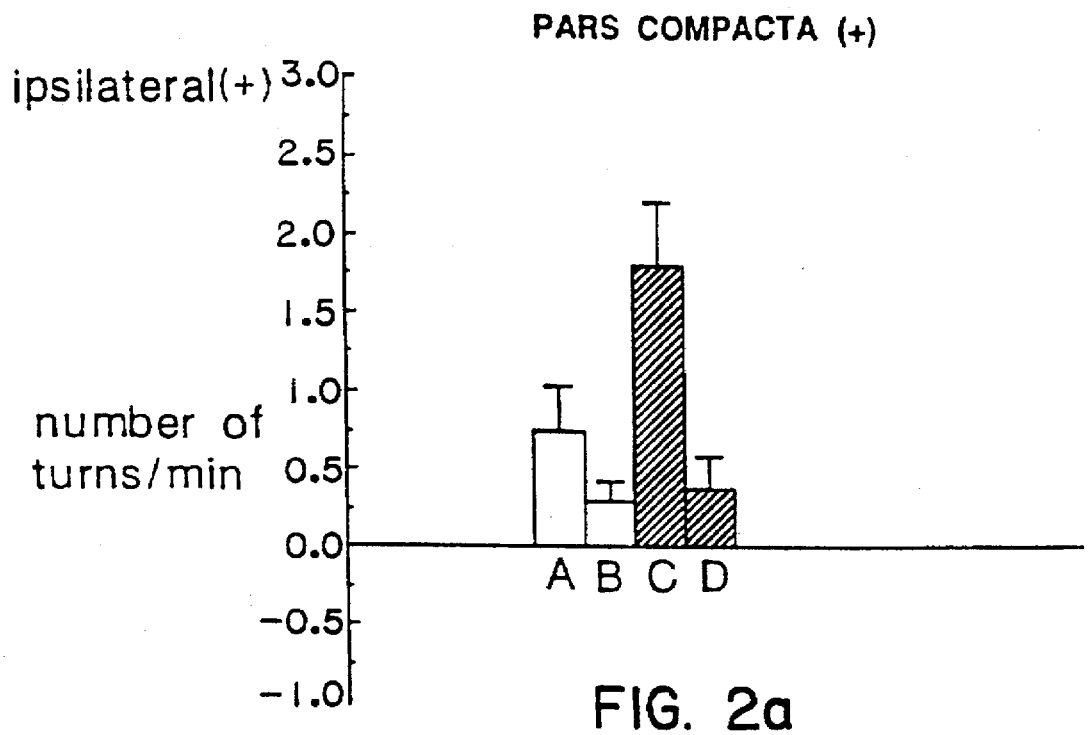
FIG. 2 shows the effects on circling behavior of tolbutamide infused into a) the pars compacta and, b) the pars reticulata, as described in Example 5.
Figure 2B:
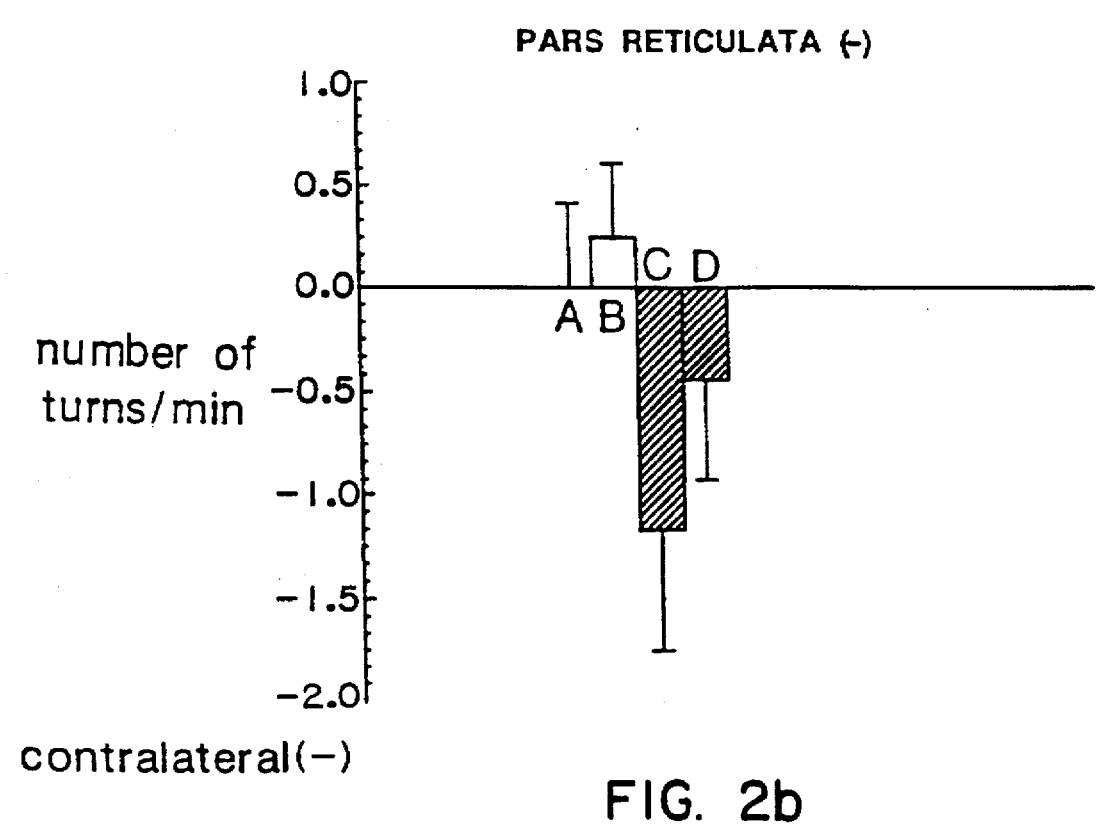

Values were calculated in each group by averaging the mean scores (±SEM) of net number of 360° turns/min from each animal FIGS. 1, 2, and 3. The effect of each drug on circling behaviour (stage C) was compared with the effect of control infusion (stage B). Statistical significance was measured using a paired Student's t-test.

RESULTS

Administration of TEA had no effect on the motor behaviour of a total of 8 rats (0.04±0.1 turns/min., NaCl infusion: 0.07±0.1 turns/min TEA infusion), FIG. 1. shows the effects of TEA on circling behaviour. Histogram shows the mean (±SEM) for four experimental stages in 8 rats in the presence of amphetamine-challenge:

(A) 3 days post implant of outer cannula (B) Immediately following infusion of NaCl vehicle (C) Following infusion of TEA Cl.

(D) Twenty four hours following (C), i.e. TEA infusion. By contrast, infusion of tolbutamide induced marked circling behaviour 'ipsiversley' or 'contraversively' i.e. either towards (1.8±0.4 turns/min) or away from (1.2±0.6 turns/min) the treated side (FIG. 2). FIG. 2 shows the effects on circling behaviour of tolbutamide infused into (a) the pars compacta for 6 rats and (b) the pars reticulata for 5 rats. In each case Histograms show circling scores for experimental stages as in legend to FIG. 1; stage C denotes immediate effects of tolbutamide. Note when drug is infused into pars compacts (a), rotation is towards the implanted side and is significant with respect to control values at the level p<0.01. When the drug is infused into the pars reticulata, turning occurs in the opposite direction to (a) i.e. away from the treated side; significant with respect to control values: p<0.05. Subsequent histological examination showed that the direction of circling corresponded to the placement of the cannulae within the substantia nigra: rats with injection cannulae implanted in the pars compacta all circled towards the treated side whereas those rotating away from the side of infusion were implanted with cannulae in the pars reticulata, (FIG. 2).

Following application of quinine, a total of 6 rats with cannulae implanted either in the pars compacta or pars reticulata displayed drug-induced circling towards the site of infusion (1.11±0.47 turns/min) significant with respect to control values: p<0.01 (FIG. 3).

Following infusion of either quinine or tolbutamide, motor behaviour reverted to pre-injection values within twenty-four hours (FIGS. 2 and 3).

The Ionic Basis of Drug-Induced Rotation

Unlike tolbutamide, application of tetraethylammonium chloride (TEA) in either the SNc or the SNr did not modify circling behaviour. TEA is known to block a wide range of potassium channels (Latorre, R. and Miller, C. (1983), J. Membrane Biol. 71:11–30). Indeed, in the concentration used in this study, TEA inhibits the voltage-activated potassium channels responsible for action potential repolarization in pars compacta cells (Llinas, R., Greenfield, S. A. and Jahnsen, H. (1984), "Electrophysiology of pars compacta cells in the in vitro substantia nigra—a possible mechanism for dendritic release," Brain Res. 294: 127–132. Nedergaard, S., Bolam, J. P. and Greenfield, S. A. (1988), "Facilitation of dendritic calcium conductance by 5-hydroxytryptamine in the substantia nigra," Nature 333: 174–177; Harris, N. C., Webb, C. and Greenfield, S. A. (1989), "A possible pacemaker mechanism in pars compacta neurons of the guinea pig substantia nigra revealed by various iopn channel blocking agents," Neuroscience 37: 355–362). It would seem then that blockade of voltage-gated potassium channels in general could not account for the circling behaviour seen.

On the other hand, TEA is not a very effective blocker of the ATP-sensitive potassium channel, (Findlay, et al., supra, 1985b). Furthermore, sulfonylureas such as tolbutamide, are effective and selective blockers of this channel (Schmid-Antomarchi, H., De Weille, J. R., Fosset, M. and Lazdunski, M. (1987), "The receptor for antidiabetic sulfonylureas controls the activity of the ATP-modulated K channel in insulin-secreting cells," J. Biol. Chem. 262: 15840–15844; Sturgess et al., supra, 1985). Since two chemically unrelated substances which caused similar and specific behavioural effects have in common the property of blocking ATP-sensitive potassium channels, the most parsimonious explanation of the drug-induced circling seen is that the ATP-sensitive potassium channel may selectively underlie a neuronal mechanism in the substantia nigra involved in the control of movement.

Specificity of Pars Compacta and Pars Reticulata

It is particularly noteworthy that application of tolbutamide resulted in circling behaviour in a direction dependent on whether the infusion was either in the pars compacta or pars reticulata. A comparable duality of behavioural response has already been reported following application of GABA to the two main sub-divisions of the substantia nigra (Coward, D. M. (1982), "Nigral actions of GABA agonists are enhanced by chronic fluphenazine and differentiated by concomittant flurazepam," Psychopharm. 76: 294–298). Furthermore, it has been demonstrated that pars compacta and pars reticulata neurons can be respectively inhibited and excited by the same substance, in this case dopamine (Waszczak, B. I. et al. (1983),"Dopamine modulation of the effects of aminobutyric acid on substantia nigra pars reticulata neurons," Science 220: 218–221). It might similarly be the case therefore that tolbutamide is having differential effects on pars compacta and pars reticulata cells. These effects could influence output pathways in two, not mutually exclusive ways: direct relays to the respective targets of compacta and reticutata cells, and/or indirect modification of pars compacta cell output via recurrent collaterals of pars reticulata cells affected by the drug, as already postulated for the GABA-induced excitation of pars compacta cells (Grace, A. A. and Bunney, B. S. (1979),"Paradoxical GABA excitation of nigral dopaminergic cells: indirect mediation through reticulata inhibitory neurons," Eur. J. Pharm. 59: 211–218). On the other hand, it is worth bearing in mind that long 'apical' dendrites extend in a dorso-ventral plane from nigrostriatal cell somata in the pars compacta into and throughout the pars reticulata (Juraska, J. M., Wilson, C. J. and Groves, P. M. (1977),"The substantia nigra of the rat: a Golgi study," J. (Comp. Neurol. 172: 585–600. Wassef, M., Berod, A. and Sotelo, c. (1981),"Dopaminergic dendrites in the pars reticulata of the rat substantia nigra and their striatal input. Combined immunocytochemistry localisation of tyrosine hydroxylase and anterograde degeneration." Neuroscience 6: 2125–2139; Greenfield, S. A. (1985), "The significance of dendritic release of transmitter and protein in the substantia nigra," Neurochem Int. 7: 887–901). Hence injections into the pars reticulata might principally entail local application of drug to pars compacta cell dendrites: the differences observed between injections in the two regions might be caused by different responses elicited from drug application to different parts of the same cell type. It appears that the membrane properties of the apical dendrites are different from those of the cell body in the pars compacta (see Nedergaard et al. supra, 1988)

Significance of ATP-sensitive Potassium Channel in Circling Behaviour

According to the model of Ungerstedt, supra (1971), contraversive circling implies that there is a relatively greater amount of available dopamine in the striatum of the treated side. Hence, the results suggest that injection of tolbutamide in the pars reticulata has the net effect of enhancing the excitability of the nigrostriatal pathway, whereas in the pars compacta quinine, and tolbutamide have caused a net decrease in striatal release of dopamine. It is surprising that a drug such as tolbutamide, which should depolarize the cell by blocking potassium efflux, appears to be an inhibitory agent. However, pars compacta cells have been shown to generate a calcium-mediated conductance that facilitates burst firing but which is deinactivated only at hyperpolarised potentials (Kita, T., Kita, H. and Kitai, S. (1986),"Electrical membrane properties of rat substantia nigra compacta neurons in an in vitro slice preparation." Brain Res. 372: 21–30). It would follow then that in these pars compacta cells, blockade of hyperpolarisation would have the paradoxical effect of a net inhibition.

SUMMARY

Application of tolbutamide and quinine, but not tetraethylammonium, caused circling behaviour. However, in the case of tolbutamide application, the direction of circling was dependent on whether the site of infusion was in the pars compacta or pars reticulata. On the other hand, the effects of quinine were the same, irrespective of site of application within the substantia nigra, that is, in the same direction as seen following injection of tolbutamide into the pars compacta. Quinine and tolbutamide are different chemical species which both, unlike tetraethylammonium, principally block the ATP-sensitive potassium channel. It therefore seems that an ATP-sensitive potassium channel in nigra cells could play a selective role in modifying the net activity of the nigrostriatal pathway, and hence the control of movement.

What is claimed is:

1. A method for treating Parkinson's disease, which comprises administering locally to a mammalian species in need of treatment a therapeutically effective amount of a sulfonyl urea which blocks an ATP-sensitive potassium channel in the brain.

2. The method as defined in claim 1, wherein the sulfonyl urea is administered to the substantia nigra of the brain.

3. The method as defined in claim 2 where the sulfonyl urea is glyburide (1-[[p-[2-(5-chloro-O-anisamido)-ethyl]phenyl]sulfonyl]-3-cyclohexylurea); chlorpropamide(1-[(p-chlorophenyl)sulfonyl]-3-propylurea); glipizide(1-cyclohexyl-3-[[p-[2-(5-methyl-pyrazinecarboxamido)ethyl]phenyl]sulfonyl]urea); tolazamide(benzenesulfonamide-N-[[(hexahydro-1H-azepin-1-yl)amino]carbonyl]-4-methyl), or tolbutamide(benzenesulfonamide, N-(butylamino)-carbonyl]-4-methyl.

4. The method as defined in claim 2 wherein the sulfonyl urea is tolbutamide.

5. The method as defined in claim 2 wherein the sulfonyl urea is administered by infusion into the substantia nigra and blocks the ATP-sensitive potassium channel.

6. The method as defined in claim 2 wherein the sulfonyl urea is administered into the pars compacta or pars reticulata.

7. The method as defined in claim 1 wherein the sulfonyl urea is administered locally by injection in the carotid artery or by lumbar puncture or cisternal puncture.

8. The method as defined in claim 1 wherein the sulfonyl urea blocks the ATP-sensitive potassium channel in the substantia nigra to modify the net activity of the nigrostriatal pathway and thus the control of movement.

9. The method as defined in claim 1 wherein the sulfonyl urea is administered locally in an amount of from about 0.1 to about 20 mg/kg/treatment.

10. A method for controlling movement of a Parkinsonian patient, which comprises administering locally to a Parkinsonian patient in need of treatment, a therapeutically effective amount of a sulfonyl urea which blocks the ATP-sensitive potassium channel in the substantia nigra to modify the net activity of the nigrostriatal pathway to control movement.

11. The method as defined in claim 10 wherein the sulfonyl urea is glyburide, chlorpropamide, glipizide, tolazamide, or tolbutamide.

12. The method as defined in claim 10 wherein the sulfonyl urea is tolbutamide.

13. The method as defined in claim 10 wherein the sulfonyl urea is administered by infusion into the substantia nigra and blocks the ATP-sensitive potassium channel.

14. The method as defined in claim 10 wherein the sulfonyl urea is administered into the pars compacta or pars reticulata.

15. The method as defined in claim 10 wherein the sulfonyl urea is administered locally by injection in the carotid artery, or by lumbar puncture or cisternal puncture.

* * * * *